US006693059B2

(12) United States Patent
Lin

(10) Patent No.: US 6,693,059 B2
(45) Date of Patent: Feb. 17, 2004

(54) PROCESS FOR PREPARING A CATALYST AND CATALYTIC OXIDATION THEREWITH

(75) Inventor: Manhua Lin, Maple Glen, PA (US)

(73) Assignee: Rohm and Haas Company, Philadelphia, PA (US)

( * ) Notice: Subject to any disclaimer, the term of this patent is extended or adjusted under 35 U.S.C. 154(b) by 412 days.

(21) Appl. No.: 09/754,942

(22) Filed: Jan. 4, 2001

(65) Prior Publication Data

US 2002/0010365 A1 Jan. 24, 2002

Related U.S. Application Data

(60) Provisional application No. 60/181,412, filed on Feb. 9, 2000.

(51) Int. Cl.[7] .......................... B01J 23/16; B01J 23/18; B01J 23/22; B01J 23/28; B01J 23/30

(52) U.S. Cl. ...................... 502/308; 502/309; 502/311; 502/312; 502/313; 502/314; 502/315; 502/316; 502/321; 502/322; 502/353

(58) Field of Search ................................ 502/104, 111, 502/113, 117, 308, 309, 311, 312, 313, 314, 315, 316, 353, 321, 322

(56) References Cited

U.S. PATENT DOCUMENTS 3,893,951 A * 7/1975 Grasselli et al. ............ 252/468
4,157,987 A * 6/1979 Dolhyj et al. ............... 252/437
4,212,767 A * 7/1980 Daniel ........................ 252/435
4,307,247 A * 12/1981 Shaw et al. ................. 562/599
4,359,407 A * 11/1982 Dolhyj et al. ............... 252/437
4,386,217 A * 5/1983 Ainbinder et al. .......... 560/207
4,485,079 A * 11/1984 Brazil, Jr. et al. .......... 423/376
4,618,593 A * 10/1986 Sasaki et al. ................. 502/20
4,746,753 A * 5/1988 Brazil, Jr. et al. .......... 558/324
4,788,317 A 11/1988 Guttmann et al.
5,380,933 A 1/1995 Ushikubo et al.
5,990,348 A 11/1999 Lyons et al.
6,013,597 A * 1/2000 Karim et al. ............... 502/209
6,060,421 A * 5/2000 Karim et al. ............... 502/303
6,084,126 A * 7/2000 Hirbst et al. ................ 562/535
6,087,297 A * 7/2000 Karim et al. ............... 502/303
6,171,998 B1 * 1/2001 Lee et al. ................... 502/304
6,180,825 B1 * 1/2001 Lin et al. .................... 562/549
6,239,325 B1 * 5/2001 Kishimoto et al. ......... 585/658
6,271,169 B1 * 8/2001 Kourtakis et al. .......... 502/305
6,350,716 B1 * 2/2002 Cook et al. ................. 502/300
6,383,977 B1 * 5/2002 Karim et al. ............... 502/311
6,500,779 B2 * 12/2002 Kourtakis et al. .......... 502/305
6,514,903 B2 2/2003 Lin et al.
6,518,216 B1 * 2/2003 Han et al. ................... 502/215

FOREIGN PATENT DOCUMENTS

DE 19717076 A1 10/1998
EP 0 389 701 10/1990
EP 0 962 253 12/1999
JP 6-228073 8/1994

* cited by examiner

*Primary Examiner*—Cam N. Nguyen

(57) ABSTRACT

A process useful for the catalytic gas phase oxidation of alkanes to unsaturated aldehydes or carboxylic acids uses catalysts of particular compositions formed in a particular manner.

6 Claims, No Drawings

PROCESS FOR PREPARING A CATALYST AND CATALYTIC OXIDATION THEREWITH

CROSS REFERENCE TO RELATED PATENT APPLICATIONS

This is a non-provisional application of prior pending U.S. provisional application Ser. No. 60/181,412 filed Feb. 9, 2000.

This invention relates to a process for preparing a catalyst and catalytic oxidation therewith. In particular, the invention relates to a process for preparing a catalyst for converting alkanes to unsaturated aldehydes and carboxylic acids, by catalytic oxidation.

Unsaturated aldehydes and carboxylic acids are important commercial chemicals. Of particular importance is (meth) acrylic acid. The highly reactive double bond and acid function of (meth)acrylic acid makes it especially suitable as a monomer which may be polymerized alone or with other monomers to produce commercially important polymers. These unsaturated acids are also useful as a starting material for esterification to produce commercially important (meth) acrylate esters. Materials derived from (meth)acrylic acid or esters of (meth)acrylic acids are useful as plastic sheets and parts, paints and other coatings, adhesives, caulks, sealants and detergents, as well as other applications.

The production of unsaturated carboxylic acids by oxidation of an olefin is well known in the art. Acrylic acid, for instance, may be commercially manufactured by the gas phase oxidation of propylene. It is also known that unsaturated carboxylic acids may also be prepared by oxidation of alkanes. For instance, acrylic acid may be prepared by the oxidation of propane. Such a process is especially desirable because alkanes generally have a lower cost than olefins. A suitable process for the oxidation of alkanes to unsaturated aldehydes or carboxylic acids which is commercially viable has yet to be achieved.

One impediment to the attainment of a commercially viable process for the catalytic oxidation of an alkane to an unsaturated carboxylic acid is the identification of a catalyst having adequate conversion and suitable selectivity, thereby providing sufficient yield of the unsaturated carboxylic acid end-product.

U.S. Pat. No. 5,380,933 discloses a method for preparing a catalyst useful in the gas phase oxidation of an alkane to an unsaturated carboxylic acid. In the disclosed method, a catalyst was prepared by combining ammonium metavanadate, telluric acid and ammonium paramolybdate to obtain a uniform aqueous solution. To this solution was added ammonium niobium oxalate to obtain a slurry. The water was removed from the slurry to obtain a solid catalyst precursor. The solid catalyst precursor was molded into a tablet, sieved to a desired particle size and then calcined at 600° C. under a nitrogen stream to obtain the desired catalyst. The resulting catalyst was asserted to be effective to convert propane to acrylic acid.

The present inventor was unable to reproduce the asserted results using the preparation method of the '933 patent. While not wishing to be bound by any theory, it is believed that the poor performance of the prior art method of the '933 patent results from the compositional or phase segregation of the component elements of the catalyst, e.g., in the slurry, between solid and liquid phases, and, during calcination, between the gas and the various solid phases.

Japanese Laid-Open Patent Application Publication No. 6-228073 discloses a method for preparing a catalyst useful in the gas phase reaction of an alkane, ammonia and oxygen to form a nitrile. In the disclosed method, a catalyst was prepared by combining ammonium metatungstenate, ammonium metavanadate and telluric acid to obtain a uniform aqueous solution. To this solution was added ammonium niobium oxalate to obtain a slurry. The solid catalyst precursor was molded into a tablet, sieved to a desired particle size and then calcined at 600° C. under a nitrogen stream to obtain the desired catalyst.

There is no disclosure, whatsoever, in the Japanese publication as to the use of such a catalyst in the catalytic oxidation of an alkane to form an unsaturated aldehyde and/or an unsaturated carboxylic acid.

The present inventor has now discovered a process for preparing a catalyst for catalyzing the gas phase oxidation of an alkane into an unsaturated aldehyde or carboxylic acid wherein phase segregation is minimized and improvements in selectivity, conversion and yield are achieved.

In one aspect of the present invention, there is provided a process for preparing a catalyst comprising: (A) admixing metal compounds, at least one of which is an oxygen-containing compound, and at least one solvent to form a solution; (B) removing the at least one solvent from the solution to obtain a catalyst precursor; and (C) calcining the catalyst precursor at a temperature of from 350° C. to 850° C. under an inert atmosphere to form a catalyst having the formula

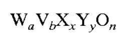

$$W_aV_bX_xY_yO_n$$

wherein a, b, x and y are molar fractions of W, V, X and Y, respectively, based on the total amount of W, V, X and Y, and n is the molar proportion of oxygen as determined by the oxidation state of W, V, X and Y, wherein a, b, x and y satisfy the following relationships $$0.25<a<0.98$$

$$0.003<b<0.5$$

$$0.003<x<0.5$$

$$0.003<y<0.5$$

wherein X is at least one element selected from the group consisting of Te, Bi, Sb and Se, and wherein Y is at least one element selected from the group consisting of Nb, Ta, Ti, Al, Zr, Cr, Mn, Fe, Ru, Co, Rh, Ni, Pd, Pt, B, In, and Ce.

In another aspect of the present invention, there is provided a process for preparing a catalyst comprising: (A) admixing metal compounds, at least one of which is an oxygen-containing compound, and at least one solvent to form a solution; (B) removing the at least one solvent from the solution to obtain a catalyst precursor; and (C) calcining said catalyst precursor at a temperature of from 350° C. to 850° C. under an inert atmosphere to form a catalyst having the formula

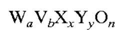

$W_aV_bX_xY_yO_n$ wherein a, b, x and y are molar fractions of W, V, X and Y, respectively, based on the total amount of W, V, X and Y, and n is the molar proportion of oxygen as determined by the oxidation state of W, V, X and Y, wherein a, b, x and y satisfy the following relationships $0.25<a<0.98$ $0.003<b<0.5$ $0.003<x<0.5$ $0.003<y<0.5$ wherein X is at least one element selected from the group consisting of Te, Bi, Sb and Se, and wherein Y is at least one element selected from the group consisting of Mo, Nb, Ta, Ti, Al, Zr, Cr, Mn, Fe, Ru, Co, Rh, Ni, Pd, Pt, B, In, and Ce, with the proviso that Mo cannot be present in a molar fraction greater than 0.20.

In additional aspects of the present invention, there are provided processes for preparing unsaturated aldehydes or carboxylic acids comprising subjecting an alkane to catalytic oxidation in the presence of a catalyst prepared according to the present invention.

As used herein, the expression "(meth)acrylic acid" is intended to include both methacrylic acid and acrylic acid within its scope. In a like manner, the expression "(meth) acrylates" is intended to include both methacrylates and acrylates within its scope.

As used herein, the terminology "($C_3$–$C_8$)alkane" means a straight chain or branched chain alkane having from 3 to 8 carbon atoms per alkane molecule.

As used herein, the term "mixture" is meant to include within its scope all forms of mixtures, e.g., simples blends, alloys, etc.

As used herein, the term "glassy precursor" is meant to include materials of a glass-like morphology, as opposed to materials having a powder morphology.

For purposes of this application, "% conversion" is equal to (moles of consumed alkane/moles of supplied alkane)×100; "% selectivity" is equal to (moles of formed desired unsaturated carboxylic acid or aldehyde/moles of consumed alkane)×100; and "% yield" is equal to (moles of formed desired unsaturated carboxylic acid or aldehyde/moles of supplied alkane)×100.

For purposes of this application, "solution" means that greater than 95 percent of a solid metal compound added to a solvent is dissolved. In this regard, it should be understood that the greater the amount of solid metal compound not initially in solution, the poorer the performance of the catalyst derived therefrom.

In a first step of the processes for preparing a catalyst, as disclosed herein, a solution is formed by admixing metal compounds, at least one of which contains oxygen, and at least one solvent in appropriate amount to form the solution. Generally, the metal compounds contain elements W, V, X, Y and O. In one embodiment, X is at least one element selected from the group consisting of Te, Bi, Sb and Se; and Y is at least one element selected from the group consisting of Nb, Ta, Ti, Al, Zr, Cr, Mn, Fe, Ru, Co, Rh, Ni, Pd, Pt, B, In and Ce. In another embodiment, X is at least one element selected from the group consisting of Te, Bi, Sb and Se; and Y is at least one element selected from the group consisting of Mo, Nb, Ta, Ti, Al, Zr, Cr, Mn, Fe, Ru, Co, Rh, Ni, Pd, Pt, B, In and Ce. In a preferred embodiment, X is at least one element selected from the group consisting of Te, Bi and Sb; and Y is at least one element selected from the group consisting of Mo, Nb, Ta, and Zr. In a more preferred embodiment, X is Te and Y is Mo and Nb.

Suitable solvents include water; alcohols including, but not limited to, methanol, ethanol, propanol and diols; and polar solvents as are known in the art. Generally, water is preferred. The water is any water suitable for use in chemical syntheses including, without limitation, distilled water and de-ionized water. The amount of solvent present is that amount sufficient to keep the elements substantially in solution long enough to avoid or minimize compositional and/or phase segregation during the preparation steps. Accordingly, the amount of solvent will vary according to the amounts and solubility of materials combined. However, as stated above, the amount of solvent must be sufficient to insure a solution is formed and not a slurry at the time of mixing.

Once the solution is formed, the water is removed by any suitable method known in the art so at form a catalyst precursor. Such methods include vacuum drying, heat evaporation, rotary evaporation, air drying and combinations thereof. Vacuum drying is generally performed at pressures ranging from 10 mmHg to 500 mmHg. Rotary evaporation is generally performed at a bath temperature of from 25° C. to 90° C. and a pressure of from 10 mmHg to 760 mmHg, preferably at a bath temperature of from 40° C. to 90° C. and a pressure of from 10 mmHg to 350 mmHg, more preferably from 40° C. to 60° C. and a pressure of from 10 mmHg to 40 mmHg. Air drying may occur at temperatures ranging from 25° C. to 90° C. It is to be understood that the faster the water removal rate, the greater the likelihood of producing a powdery precursor rather than a glassy precursor. A glassy precursor has been found to be desirable in terms of yielding a superior catalyst.

Once obtained, the catalyst precursor is calcined under an inert atmosphere. The inert atmosphere may be any material which is substantially inert, i.e., does not react or interact with, the catalyst precursor. Suitable examples include, without limitation, nitrogen, argon, xenon, helium or mixtures thereof. Preferably, the inert atmosphere is argon or nitrogen, more preferably nitrogen. The inert atmosphere may flow over the surface of the catalyst precursor or may not flow thereover (i.e., a static environment). It is important to understand that by a non-flow atmosphere it is meant that, while the inert gas covers and surrounds the catalyst precursor glass, the inert gas is not allowed to flow over the surface of the catalyst precursor glass. It is preferred that the inert atmosphere not flow over the surface of the catalyst precursor. However, when the inert atmosphere does flow over the surface of the catalyst precursor, the flow rate can vary over a wide range, for example, over a space velocity range of from 1 to 500 $hr^{-1}$.

The calcination is typically done at a temperature of from 350° C. to 850° C., preferably from 400° C. to 700° C., more preferably from 500° C. to 640° C. The calcination is performed for an amount of time suitable to convert the catalyst precursor into the catalyst. Generally, the calcination may be performed for from 0.5 to 30 hours, preferably from 1 to 25 hours, and more preferably from 1 to 15 hours.

With calcination, catalysts are formed having the formula

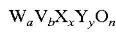

$$W_aV_bX_xY_yO_n$$

wherein X, Y, a, b, x, y and n are all as described above.

The molar proportion, n, i.e., the amount of oxygen (O) present, is dependent on the oxidation state of the other elements in the catalyst. However, typically, n is from 3 to 4.7 based on the other elements present in the catalyst and their relative proportions.

The so-formed catalysts may be used as a solid catalyst alone or may be utilized with a suitable support, such as, without limitation, silica, alumina, titania, aluminosilicates, diatomaceous earth or zirconia. The shape of the catalyst can be any suitable shape and may depend upon the particular application of the catalyst. In a like manner, the particle size of the catalyst may be any suitable particle size depending on the particular use of the catalyst.

A further aspect of the present invention is a process for preparing an unsaturated aldehyde and/or an unsaturated carboxylic acid including subjecting an alkane to catalytic oxidation in the presence of a catalyst prepared according to the present invention.

The starting materials are generally an alkane gas or gases and at least one oxygen-containing gas. It is preferred that the starting materials also include water, i.e., water vapor, e.g., steam. Accordingly, a starting material gas is supplied to the reactor which includes a gas mixture of at least one alkane and steam. The at least one oxygen-containing gas may be included in this mixture or may be supplied separately. Furthermore, a diluting gas, such as an inert gas, including without limitation, nitrogen, argon, helium or carbon dioxide may also be included. The diluting gas may be used to dilute the starting material and/or to adjust the space velocity, the oxygen partial pressure and the steam partial pressure.

Suitable molar ratios of alkane/oxygen/diluting gas/water are known in the art. For example, the molar ratio of alkane/oxygen/diluting gas/water in the starting material may be 1/0.1 to 10.0/0 to 20/0.2 to 70, more preferably, 1/1 to 5.0/0 to 10/5 to 40.

The starting material alkane is generally any alkane suitable for gas phase oxidation into an unsaturated aldehyde or carboxylic acid. Generally, the alkane is a $C_3$–$C_8$ alkane, preferably propane, isobutane or n-butane, more preferably propane or isobutane, most preferably propane. Furthermore, the alkane may be a mixture of alkanes including $C_3$–$C_8$ alkanes as well as lower alkanes such as methane and ethane.

The process may use pure oxygen gas, an oxygen-containing gas such as air, an oxygen enriched gas, or a mixture thereof.

In a preferred embodiment, the starting material is a gas mixture of propane, air and steam. The starting gas mixture is subjected to catalytic oxidation in the presence of the catalyst of the present invention. The catalyst may be in a fluidized bed or a fixed bed reactor. The reaction is generally conducted under atmospheric pressure, but may be conducted under elevated or reduced pressure. The reaction temperature is generally from 200° C. to 550° C., preferably 300° C. to 480° C., more preferably 350° C. to 440° C. The gas space velocity is generally 100 to 10,000 $hr^{-1}$, preferably 300 to 6,000 $hr^{-1}$, more preferably 300 to 3,000 $hr^{-1}$.

Also, in the method of the present invention it is to be understood that an unsaturated aldehyde may also be formed. For instance, when propane is the starting alkane, acrolein may be formed; and when isobutane is the starting alkane, methacrolein may be formed.

EXAMPLE 1

A catalyst having the formula of $W_1V_{0.3}Te_{0.23}Nb_{0.12}O_n$ was prepared as follows: 36.26 g of ammonium metatungstenate (Aldrich) having 68.6 wt % of W, 4.80 g of ammonium metavanadate (Alfa) and 7.22 g of telluric acid (Aldrich) were added to a flask containing 520 g of deionized water (Milli-Q). A uniform solution was formed by heating and stirring at 80° C. The solution was cooled to about 30° C. and 169.4 g of ammonium niobium oxalate was added thereto and dissolved therein. About 160 g of the resulting solution was evaporated slowly at about 50° C. under reduced pressure (260 mmHg), with agitation, to obtain a dry precursor. The drying was continued in a vacuum oven over night to obtain about 11 g of a glassy catalyst precursor. Under a nitrogen atmosphere, about 2.6 g of the precursor was preheated to 200° C. for 1 hour and then calcined at 600° C. for 2 hours in a closed system. The resulting catalyst was crushed so as to pass through a 20-mesh sieve.

1 g of the resulting catalyst was packed in a quartz tube (4 mm ID) and fed with a gas mixture of propane, air and steam (molar ratio of propane/air/steam=1/96/3) at a fixed space velocity of 1440 $hr^{-1}$, under ambient pressure at a reaction temperature of 350° C. The results are set forth in Table 1.

EXAMPLES 2–6

These catalysts were prepared in the same manner as described in Example 1. The evaluation conditions were also the same as in Example 1, except for the variation of the evaluation temperature as indicated. The results are set forth in Table 1.

EXAMPLE 7

The catalyst was prepared in the same manner as described in Example 1, except that molybdenum (ammonium heptamolybdate tetrahydrate (Aldrich)) was also incorporated into the catalyst. The evaluation conditions are the same as in Example 1, except for the variation of the evaluation temperature as indicated. The results are set forth in Table 1.

COMPARATIVE EXAMPLE C1

The catalyst was prepared in the same manner as described in Example 1, except that W was replaced by Nb. The evaluation conditions are the same as in Example 1, except for the variation of the evaluation temperature as indicated. The results are set forth in Table 1.

COMPARATIVE EXAMPLE C2

The catalyst was prepared in the same manner as described in Example 1, except that W was replaced by Fe (iron nitrate nonahydrate (Aldrich)). The evaluation conditions are the same as in Example 1, except for the variation of the evaluation temperature as indicated. The results are set forth in Table 1.

COMPARATIVE EXAMPLE C3

The catalyst was prepared in the same manner as described in Example 1. The evaluation conditions are the same as in Example 1, except for the use of a gas mixture of propane and air (molar ratio of propane/air=1/99). The results are set forth in Table 1.

COMPARATIVE EXAMPLE C4

The catalyst was prepared in the same manner as described in Example 1, except that the calcination was carried out under an atmosphere of air rather than nitrogen. The evaluation conditions are the same as in Example 1, except for the variation of the evaluation temperature as indicated. The results are set forth in Table 1.

COMPARATIVE EXAMPLES C5–C8

The catalysts were prepared in the same manner as described in Example 1, except that one metal was absent in each catalyst. The evaluation conditions are the same as in Example 1, except for the variation of the evaluation temperature as indicated. The results are set forth in Table 1.

COMPARATIVE EXAMPLE C9

The catalyst was prepared in the same manner as described in Example 1, except that the only metals utilized were W and V. The evaluation conditions are the same as in Example 1. The results are set forth in Table 1.

TABLE 1

| | Composition | Temp. (° C.) | Conv. (%) | Select. (%) | Yield (%) |
|---|---|---|---|---|---|
| 1 | $W_1V_{0.3}Te_{0.23}Nb_{0.12}O_n$ | 350 | 18 | 19 | 3.5 |
| 2 | $W_1V_{0.3}Te_{0.23}Nb_{0.12}O_n$ | 380 | 33 | 8 | 2.6 |
| 3 | $W_1V_{0.45}Te_{0.35}Nb_{0.18}O_n$ | 350 | 12 | 32 | 3.8 |
| 4 | $W_1V_{0.45}Te_{0.35}Nb_{0.18}O_n$ | 380 | 20 | 14 | 2.9 |
| 5 | $W_1V_{0.25}Te_{0.49}Nb_{0.30}O_n$ | 380 | 12 | 24 | 2.8 |
| 6 | $W_1V_{0.19}Te_{0.24}Nb_{0.14}O_n$ | 350 | 19 | 16 | 3 |
| 7 | $W_1V_{0.45}Te_{0.35}Nb_{0.18}Mo_{0.2}O_n$ | 350 | 9 | 61 | 5.5 |
| C1 | $Nb_{1.12}V_{0.3}Te_{0.23}O_n$ | 380 | 1 | 0 | 0 |
| C2 | $Fe_1V_{0.3}Te_{0.23}Nb_{0.12}O_n$ | 380 | 5 | 0 | 0 |
| C3 | $W_1V_{0.3}Te_{0.23}Nb_{0.12}O_n$ | 350 | 15 | 11 | 1.6 |
| C4 | $W_1V_{0.25}Te_{0.49}Nb_{0.30}O_n$ | 380 | 0 | | |
| C5 | $V_{0.25}Te_{0.49}Nb_{0.30}O_n$ | 380 | 0 | | |
| C6 | $W_1Te_{0.49}Nb_{0.30}O_n$ | 380 | 0 | | |
| C7 | $W_1V_{0.25}Nb_{0.30}O_n$ | 350 | 71 | | 0.4 |
| C8 | $W_1V_{0.25}Te_{0.49}O_n$ | 380 | 0 | | |
| C9 | $W_1V_{0.25}O_n$ | 350 | 49 | | 0.3 |

EXAMPLES 8–16

The catalysts were prepared in the same manner as described in Example 1, except as otherwise indicated. The evaluation conditions were also the same as in Example 1, except as otherwise indicated. The results are set forth in Table 2.

COMPARATIVE EXAMPLES C10–C14

The catalysts were prepared in the same manner as described in Example 1, except as otherwise indicated. The evaluation conditions were also the same as in Example 1, except as otherwise indicated. The results are set forth in Table 2.

TABLE 2

| | Composition | T (° C.) | C (%) | S (%) | Y (%) | Feed P/air/$H_2O$ | Drying |
|---|---|---|---|---|---|---|---|
| 6 | $W_1V_{0.19}Te_{0.24}Nb_{0.14}O_n$ | 350 | 18.6 | 16.7 | 3.1 | 1/96/3 | (2) |
| C10 | " | 380 | 0.5 | — | 0.06 | 1/96/3 | (1) |
| C11 | " | 380 | 1.5 | — | 0.33 | 7/70/23 | (1) |
| 8 | " | 380 | 35 | 3.8 | 1.3 | 7/70/23 | (3) |
| 9 | $W_1V_{0.25}Te_{0.49}Nb_{0.30}O_n$ | 380 | 8.3 | 45.8 | 3.8 | 1/96/3 | (2) |
| C12 | " | 380 | 0.3 | — | 0.17 | 1/96/3 | (1) |
| C13 | " | 380 | 0.9 | — | 0.06 | 7/70/23 | (1) |
| 10 | " | 378 | 14 | 11 | 1.5 | 7/70/23 | (3) |
| 11 | $W_1V_{0.45}Te_{0.35}Nb_{0.18}O_n$ | 350 | 18 | 12 | 2.2 | 7/70/23 | (3) |
| 12 | " | 350 | 23 | 8 | 1.8 | 1/96/3 | (3) |
| 13 | " | 350 | 11 | 12 | 1.3 | 1/96/3 | (1) |
| 14 | " | 350 | 12 | 15 | 1.8 | 1/96/3 | (2) |
| 15 | " | 350 | 21 | 11 | 2.3 | 1/96/3 | (4) |
| 16 | " | 350 | 7 | 31 | 2.2 | 1/96/3 | (5) |
| C14 | " | 350 | 4 | 22 | 0.9 | 1/96/3 | (6) |

T = reaction temperature; C = conversion; S = selectivity; Y = yield; P = propane
(1) Rotavap - bulk of water removed in 3–4 hours - performance inconsistent - powdery catalyst precursor sometimes
(2) Rapidvap - bulk of water removed in >16 hours - glassy precursor
(3) Rotavap-Air - rotavap to remove >95% of water in 3–4 hours, followed by air-drying (about 2 days) to obtain glassy precursor
(4) Air-dry - produces consistent glassy precursor
(5) Heat evaporation - can produce glassy precursor with careful control of evaporation/agitation rates
(6) Freeze dry - generates powdery precursors

EXAMPLE 17

The catalyst was prepared in the same manner as described in Example 1, except as otherwise indicated. The evaluation conditions were also the same as in Example 1, except as otherwise indicated. The results are set forth in Table 3.

COMPARATIVE EXAMPLES C15–C19

The catalysts were prepared in the same manner as described in Example 1, except as otherwise indicated. The evaluation conditions were also the same as in Example 1, except as otherwise indicated. The results are set forth in Table 3.

TABLE 3

| | Composition | T (° C.) | C (%) | S (%) | Y (%) | Feed P/air/$H_2O$ | Drying |
|---|---|---|---|---|---|---|---|
| 7 | $W_1V_{0.45}Te_{0.35}Nb_{0.18}Mo_{0.2}O_n$ | 350 | 9 | 61 | 5.5 | 1/96/3 | (2) |
| 17 | $W_1V_{0.45}Te_{0.35}Nb_{0.18}O_n$ | 350 | 34 | 7.4 | 2.5 | 1/96/3 | (2) |
| C15 | $V_{0.45}Te_{0.35}Nb_{0.18}O_n$ | 350 | 0 | | | 1/96/3 | (2) |
| C16 | $W_1Te_{0.35}Nb_{0.18}O_n$ | 350 | 0 | | 0 | 1/96/3 | (2) |
| C17 | $W_1V_{0.45}Nb_{0.18}O_n$ | 350 | 65 | | 0.2 | 1/96/3 | (2) |
| C18 | $W_1V_{0.45}Te_{0.35}O_n$ | 350 | 19 | | 0.1 | 1/96/3 | (2) |
| C19 | $W_1V_{0.45}O_n$ | 350 | 88 | | 0.2 | 1/96/3 | (2) |

T, C, S, Y, P, (1), (2), (3), (4), (5) and (6) all have the same meaning as in Table 2.

EXAMPLES 18–22

Catalysts having the formula $W_1V_{0.45}Te_{0.35}Nb_{0.18}O_n$ were prepared in the same manner as described in Example 1, except for the noted differences in drying technique. The evaluation conditions were also the same as in Example 1. The results are shown in Table 4.

COMPARATIVE EXAMPLES C20–C24

Catalysts were prepared in the same manner as in Examples 18–22, respectively, except for the formation of a slurry rather than a solution during the initial mixing of components. The evaluation conditions were also the same as in Example 1. The results are shown in Table 4.

TABLE 4

| | Drying | P Conversion (%) |
|---|---|---|
| 18 | (3) | 23 |
| C20 | " | 15 |
| 19 | (1) | 11 |
| C21 | " | 11 |
| 20 | (2) | 12 |
| C22 | " | 3 |
| 21 | (4) | 21 |
| C23 | " | 12 |
| 22 | (5) | 7 |
| C24 | " | 1 |

P, (1), (2), (3), (4) and (5) all have the same meaning as in Table 2.

EXAMPLES 23 AND 24

Catalysts were prepared in the same manner as described in Example 1, except as otherwise indicated. The evaluation conditions were also the same as in Example 1, except as otherwise indicated. The results are set forth in Table 5.

COMPARATIVE EXAMPLES C25–C29

Catalysts were prepared in the same manner as described in Example 1, except as otherwise indicated. The evaluation conditions were also the same as in Example 1, except as otherwise indicated. The results are set forth in Table 5.

TABLE 5

| | Composition | T (° C.) | C (%) | S (%) | Y (%) | Feed P/air/$H_2O$ | Calcination |
|---|---|---|---|---|---|---|---|
| 5 | $W_1V_{0.25}Te_{0.49}Nb_{0.30}O_n$ | 380 | 12 | 24 | 2.8 | 1/96/3 | $N_2$, covered |
| C25 | " | " | 0 | | 0 | " | air, covered |
| C26 | " | " | 0 | | 0 | " | air, open |
| 23 | $W_1V_{0.19}Te_{0.24}Nb_{0.14}O_n$ | 380 | 28 | 10 | 2.9 | 1/96/3 | $N_2$, covered |
| C27 | " | " | 0 | | 0 | " | air, covered |
| 24 | $W_1V_{0.27}Te_{0.09}Nb_{0.13}O_n$ | 380 | 98 | | 0.3 | 1/96/3 | $N_2$, covered |
| C28 | " | " | 0.8 | | 0 | " | air, covered |
| C29 | " | " | 0.2 | | 0 | " | air, open |

T, C, S, Y and P all have the same meaning as in Table 2.

EXAMPLE 25

A catalyst was prepared in the same manner as described in Example 1, except as otherwise indicated. The evaluation conditions were also the same as in Example 1, except as otherwise indicated. The results are set forth in Table 6.

COMPARATIVE EXAMPLES C30 AND C31

Catalysts were prepared in the same manner as described in Example 1, except as otherwise indicated. The evaluation conditions were also the same as in Example 1, except as otherwise indicated. The results are set forth in Table 6.

TABLE 6

| | Composition | T (° C.) | C (%) | S (%) | Y (%) | Feed P/air/$H_2O$ |
|---|---|---|---|---|---|---|
| 1 | $W_1V_{0.3}Te_{0.23}Nb_{0.12}O_n$ | 350 | 18 | 19 | 3.5 | 1/96/3 |
| C30 | " | " | 15 | 11 | 1.6 | 1/96/0 |
| 25 | $W_1V_{0.45}Te_{0.35}Nb_{0.18}O_n$ | 350 | 27 | 12 | 3.3 | 1/96/3 |
| C31 | " | " | 16 | 10 | 1.6 | 1/96/0 |

T, C, S, Y and P all have the same meaning as in Table 2.

What is claimed:

1. A process for preparing a catalyst comprising:

(A) admixing metal compounds, at least one of which is an oxygen-containing compound, and at least one solvent to form a solution, (B) removing said at least one solvent from the solution to obtain a catalyst precursor, and (C) calcining said catalyst precursor at a temperature of from 350° C. to 850° C. under an inert atmosphere to form a catalyst having the formula $$W_aV_bX_xY_yO_n$$

wherein a, b, x and y are molar fractions of W, V, X and Y, respectively, based on the total amount of W, V, X and Y, and n is the molar proportion of oxygen as determined by the oxidation state of W, V, X and Y, wherein a, b, x and y satisfy the following relationships $$0.25<a<0.98$$

$$0.003<b<0.5$$

$$0.003<x<0.5$$

$$0.003<y<0.20$$

wherein X is at least one element selected from the group consisting of Te, Bi, Sb and Se, wherein Y comprises Mo.

2. The process according to claim 1, wherein said at least one solvent is water.

3. The process according to claim 1, wherein Y is a mixture of Nb and Mo.

4. The process claim 1, wherein the inert atmosphere is not flowing over the surface of the catalyst precursor during calcination.

5. A process for preparing a catalyst comprising:

(A) admixing metal compounds, at least one of which is an oxygen-containing compound, and at least one solvent to form a solution, (B) removing said at least one solvent from the solution to obtain a catalyst precursor, and (C) calcining said catalyst precursor at a temperature of from 350° C. to 850° C. under an inert atmosphere to form a catalyst comprising:

Mo present in a molar fraction not greater than 0.20;

V present in a molar fraction from 0.003 to 0.5;

at least one of Te, Bi, Sb, or Se present in a molar fraction from 0.003 to 0.5; and at least one of Nb, Ta, Ti, Al, Zr, Cr, Mn, Fe, Ru, Co, Rh, Ni, Pd, Pt, B, In, or Ce present in a molar fraction from 0.003 to 0.5.

6. A process for preparing a catalyst comprising:

(A) admixing metal compounds, at least one of which is an oxygen-containing compound, and at least one solvent to form a solution, (B) removing said at least one solvent from the solution to obtain a catalyst precursor, and (C) calcining said catalyst precursor at a temperature of from 350° C. to 850° C. under an inert atmosphere to form a catalyst comprising:

W present in a molar fraction from 0.25 to 0.98;

Mo present in a molar fraction not greater than 0.20;

V present in a molar fraction from 0.003 to 0.5;

at least one of Te, Bi, Sb, or Se present in a molar fraction from 0.003 to 0.5; and at least one of Nb, Ta, Ti, Al, Zr, Cr, Mn, Fe, Ru, Co, Rh, Ni, Pd, Pt, B, or In, or Ce present in a molar fraction from 0.003 to 0.5.

* * * * *